United States Patent [19]

Lemieux

[11] Patent Number: 5,108,374

[45] Date of Patent: Apr. 28, 1992

[54] STICKLESS CATHETER WITH MANUAL SHUT-OFF VALVE

[75] Inventor: Francis P. Lemieux, Palm Harbor, Fla.

[73] Assignee: Critikon, Inc., Fla.

[21] Appl. No.: 517,996

[22] Filed: May 2, 1990

[51] Int. Cl.$^5$ .................................... A61M 5/178
[52] U.S. Cl. .................................... 604/164; 604/264
[58] Field of Search .............. 604/164, 167, 169, 192, 604/198, 263, 264, 280, 245, 246, 250, 119, 30, 31, 32, 33, 34

[56] References Cited

U.S. PATENT DOCUMENTS

| | | | |
|---|---|---|---|
| 4,655,214 | 4/1987 | Linder | 604/165 |
| 4,735,614 | 4/1988 | Yapp et al. | 604/165 |
| 4,784,156 | 11/1988 | Gary | 604/169 |
| 4,804,365 | 2/1989 | Litzie et al. | 604/280 |
| 4,842,591 | 6/1989 | Luther | 604/167 |
| 4,850,961 | 7/1989 | Wanderer et al. | 604/263 |
| 4,960,259 | 10/1990 | Sumanvader et al. | 604/250 |
| 5,030,205 | 7/1991 | Holdaway et al. | 604/164 |

Primary Examiner—C. Fred Rosenbaum
Assistant Examiner—M. Mendez
Attorney, Agent, or Firm—Paul A. Coletti

[57] ABSTRACT

A catheter device is described with a safety needle guard that covers and protects the needle after use of the device. The device includes a semi-tubular needle housing containing a flash chamber with a hollow needle extending from the distal end of the flash chamber. A tubular needle guard concentrically fits and slides within the needle housing. The needle guard has a longitudinal slot through which the mounting base of the flash chamber passes as the guard slides within the housing. The top of the semi-tubular housing is open so that a user may access the top of the tubular needle guard with a finger to urge the needle guard to an extended position from the distal end of the housing and in a surrounding position about the needle. The proximal end or hose of the needle guard detaches for the needle housing and has a luer fitting for an infusion set. The catheter hub contains a lever capable of occluding the catheter to inhibit fluid flow.

13 Claims, 3 Drawing Sheets

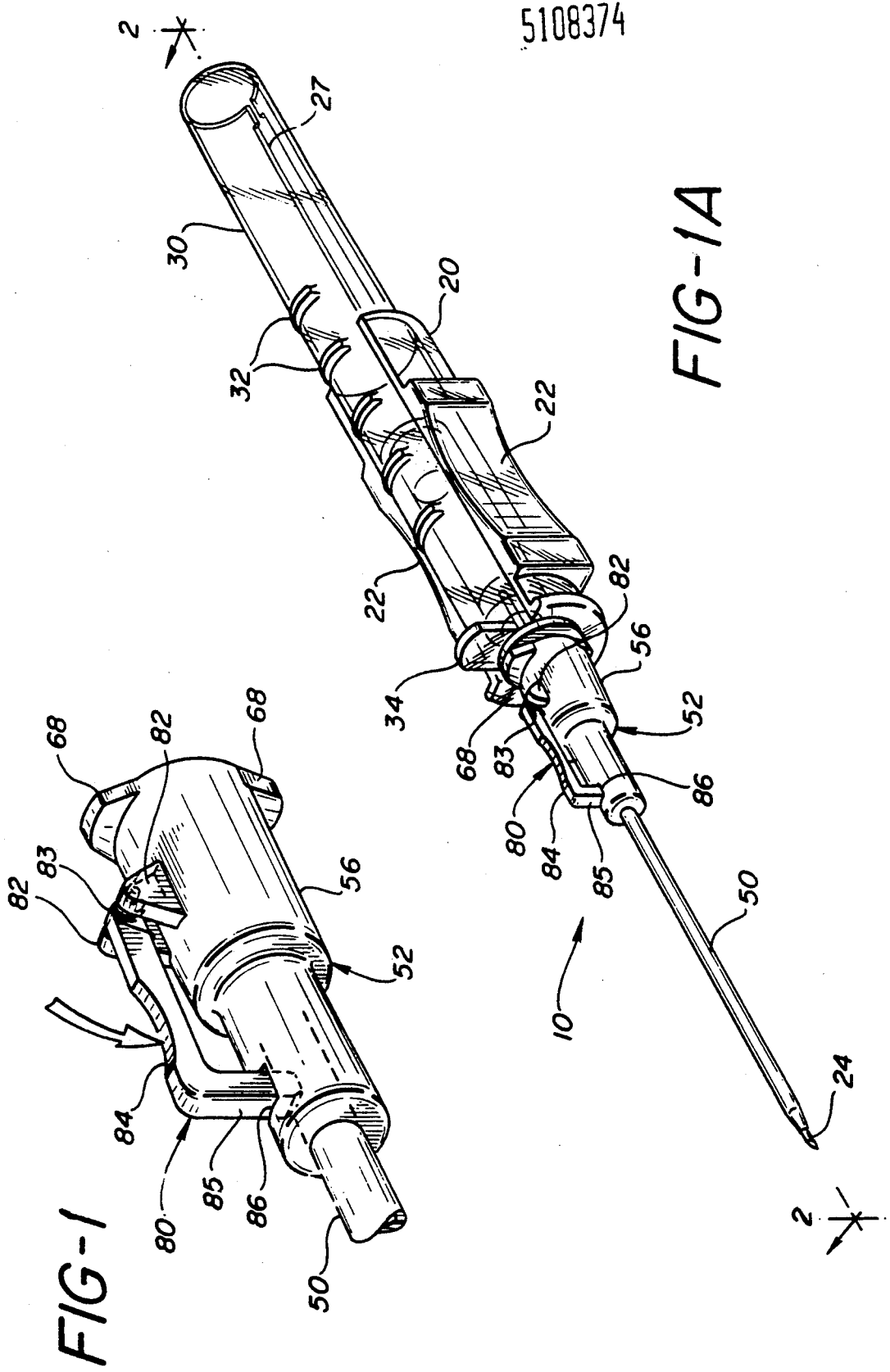

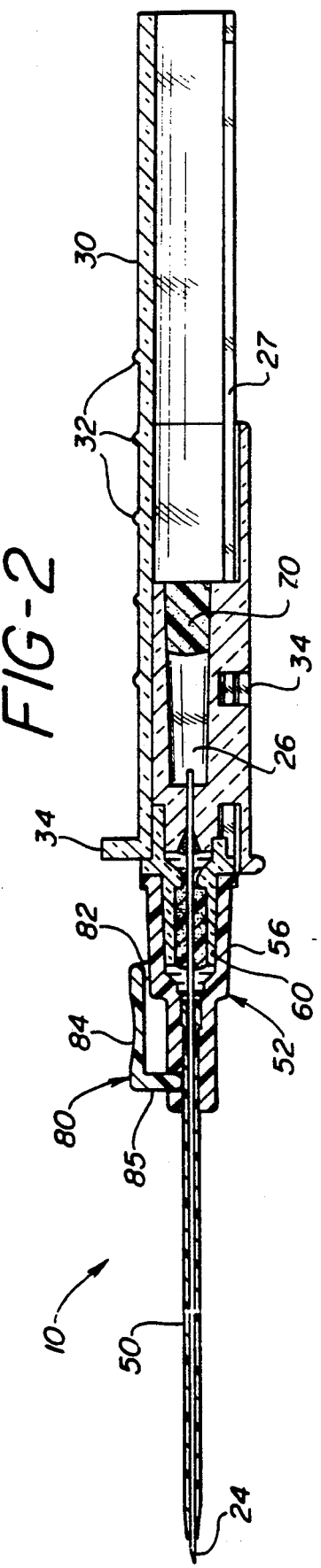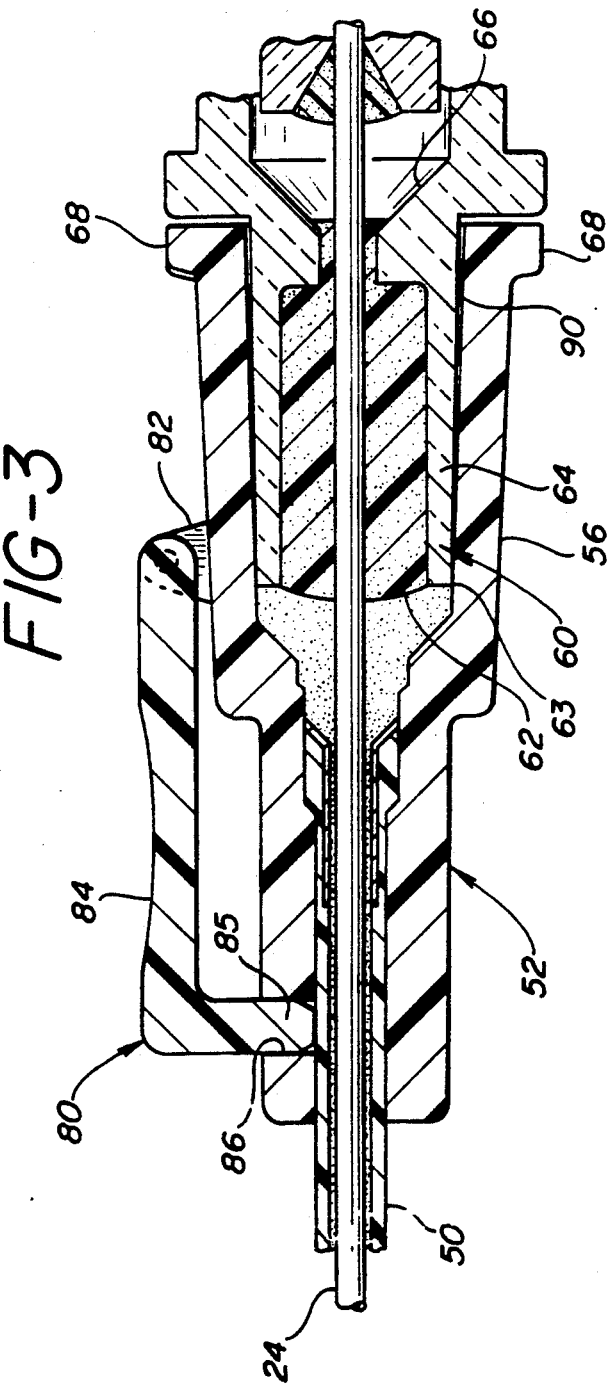

STICKLESS CATHETER WITH MANUAL SHUT-OFF VALVE

This invention relates to intravascular (I.V.) catheters and, in particular, to I.V. catheter assemblies which cover the needle Point after use to prevent accidental injury from used needles. More particularly, this invention relates to the fluid flow from the catheter to a catheter hub assembly, and a means to manually close such flow.

Intravenous catheters for the infusion of fluids into the peripheral veins of a patient are one of the most common devices used in I.V. therapy. I.V. catheters may be produced in two general forms: through-the-needle catheters, in which a catheter is threaded through the needle cannula and into the vein of a patient, and over-the-needle catheters, in which the needle and concentric outer catheter are inserted into the vein and the needle is withdrawn through the emplaced catheter.

A typical over-the-needle I.V. catheter assembly requires the user to remove and then dispose of a contaminated needle after the needle tip and catheter are properly located in a blood vessel of a patient. Once the needle is withdrawn from the catheter, the user's immediate priorities are infusion set connection and site preparation, including the taping of the catheter to the patient. Because of the urgency of these procedures, the needle is normally just dropped conveniently nearby and then retrieved later. Since the needle at this time is exposed and located close to where the user is completing work with the catheter, accidental self-inflicted needle injuries are not uncommon. For reasons of the desirability of protecting the user from exposure to blood borne disease such as hepatitis and AIDS, there is an increasing need to protect the user from accidental needle injury.

A catheter design which is directed toward this need is shown in U.S. Pat. No. 4,762,516. The catheter shown in this application includes an elongate body which houses a sliding needle guard. In use, the needle with its surrounding catheter tube is inserted through the skin of a patient until the tip of the needle is located in a blood vessel, a position detected by a small flow of blood through the needle and into the flash chamber of the catheter. The user then advances a tab on the top of the needle guard to simultaneously thread the catheter tube into the blood vessel and begin the retraction of the needle from the catheter tube. As the needle is withdrawn from the emplaced catheter, the advance of the tab slides the needle guard out of the housing and along the needle, until the distal end of the guard covers the needle tip and the proximal end of the guard locks in the elongate body. The needle and guard may then be set aside with the needle tip fully protected.

It is also desirable to provide such a catheter in a smaller, smoothly operating configuration which can be readily manipulated by small hands. In accordance with U.S. Ser. No. 335,472, now U.S. Pat. No. 5,000,740, and catheter assembly with needle guard is provided with a semi-tubular needle housing that is open on the upper surface. Located within the housing is a flash chamber with a needle extending from the distal end of the chamber and beyond the distal end of the housing. A tubular needle guard is located for distal movement within the semi-tubular needle housing, and has a distal opening through which the needle extends. The bottom of the needle guard is slotted to fit around the base of the flash chamber. At the rear of the needle guard slot is a portion of a locking mechanism which will engage with and lock in the needle housing when the needle guard is extended to cover the needle.

While these previously mentioned disclosures effectively operate to cover the needle after removal from the catheter hub assembly, they are somewhat lacking in their ability to prevent seepage of blood while the needle is inserted through the catheter or cannula and into the patient. Normally during insertion, blood flows through the cannula into a flash chamber in the needle assembly. Naturally, blood will flow into the flash chamber until the chamber is full. A porous barrier permits breathing of the flash chamber, and yet prevents blood from leaking through the back of the flash chamber.

In previous designs it would be likely for the blood to flow out of the needle nose and into the void distal area of the catheter hub. In fact, some of the needle/hub assembly configurations increase this likelihood in that the catheter hub and needle nose had a clearance designed between them. This clearance was created for two reasons. First, it was desirable for the needle nose base to be fully seated within the distal end of the hub to assure proper placement of the needle and catheter within the patient.

Second, it was desirable to create a clearance so that during withdrawal of the needle guard from the catheter, there would be no increased force needed to disconnect the needle from the catheter. This made it possible for blood to leak out of the catheter hub or flow through the needle nose to leak within the catheter.

If the catheter contained a gasket at the tip of the needle nose, blood was prevented from being pulled within the needle guard and therefore could leak from only one location, the proximal end of the needle hub. Although such leakage is a rather common phenomenon for an intra I.V. catheter, blood leakage is not a desirable situation, since this may cause inadvertent blood contact, and also make locking and withdrawal of a needle guard more troublesome.

One method of resolving this difficulty was accomplished in U.S. Ser. No. 5,000,740 which discloses a catheter assembly wherein the I.V. catheter device has standard catheter with luer connecting hub, a slidable needle housing and an extendable needle guard. The nose tip of the needle guard is designed to create a positive interference with the catheter hub assembly, so that the hub/catheter and the needle guard act as one unit. This interference fit causes a sealing effect between the catheter hub and needle nose assembly. It further allows the needle nose to be fully seated within the catheter hub to maintain accurate control of the distance between the catheter tip and the beveled portion of the needle.

Even this configuration, however, does not allow the user a manual override of the entire system. For instance, if the user has determined that blood seepage is entirely unacceptable, or that infusion should be stopped immediately, there is no mechanism to allow such shutoff without the removal of the catheter itself. Naturally, removal of the catheter requires a much greater manual exercise than the mere shutoff of flow through the catheter. Therefore, while certain refinements have existed in past catheters, none of the foregoing catheter assemblies provide for shutoff during flow.

SUMMARY OF THE INVENTION

It is an object of the invention to provide a manual seal in a catheter assembly.

It is yet another object of the invention to provide a catheter assembly which prevents blood leakage during insertion of the needle into the patient.

It is yet another object of the invention to provide a catheter in which blood accumulates only in the flash chamber of the catheter assembly until disconnection of the needle from the catheter assembly, and such collection of blood is controllable by the user.

Finally, it is an object of the invention to provide an assembly where flow through the catheter can be manually controlled during either insertion or during infusion.

These and other objects of the invention are accomplished in a catheter assembly where the catheter hub contains a pivotable, manually operable mechanism capable of pinching the catheter tube and closing the fluid path. The mechanism generally comprises a finger-like insert which is passed through a slot in the catheter hub assembly and can come into direct manual contact with the catheter. The closing mechanism is held in an open position by a spring, and must be mechanically moved to a closed position by pivoting around the pivot point. The catheter is formed from a kink-resistant material, usually a polyurethane, so that after the catheter closing mechanism is placed into an open position, the catheter returns to its unoccluded position and flow again begins.

The invention will be better understood from the following drawings and Detailed Description of the Invention.

DETAILED DESCRIPTION OF THE DRAWINGS

Figure 3A:
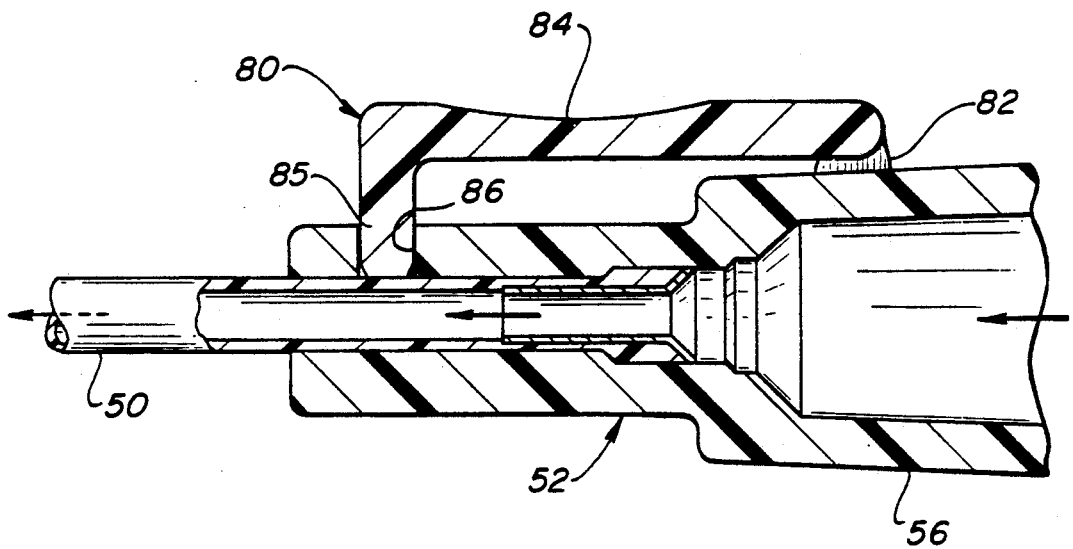
Figure 3B:
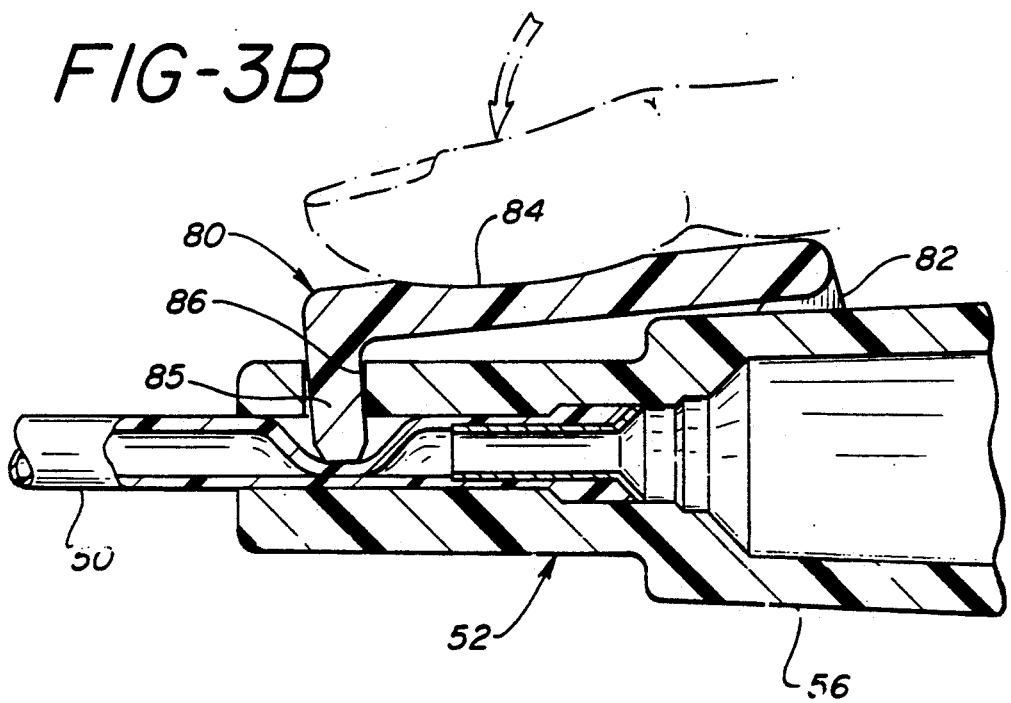

FIGS. 1 and 1a are perspective views of a catheter assembly constructed in accordance with the principles of the present invention;

FIG. 2 is a cross-sectional view of the catheter assembly taken along lines 2—2 of FIG. 1; and FIGS. 3, 3a and 3b are cross-sectional views of the manual shutoff of this invention for use with the catheter assembly of FIGS. 1 and 2.

Referring first to FIGS. 1 and 1a, a catheter assembly 10 constructed in accordance with the principles of the present invention is shown. The assembly 10 includes a needle housing 20 which is semi-tubular in shape and open at the top. Molded on the sides of the needle housing 20 are opposing contoured finger grips 22, one of which is visible in FIG. 1. Located inside the semi-tubular needle housing and extending proximally therefrom is a tubular needle guard 30. On the upper surface of the needle guard are a number of small projections 32 which provide surfaces against which a user may press to fully extend the needle guard. These projections permit a user to extend the needle guard with the index or other finger while holding the catheter assembly with one hand. Extending distally from the needle housing 20 is a protective sheath (not shown) which covers the distally extending needle and catheter.

The catheter 50 and its catheter hub 52 are mounted on the distal end of the needle guard 30. The point of the needle 24 is seen to extend from the distal tip of the catheter 50. A push-off tab 34 is seen projecting upward from the needle guard proximal the catheter hub 52. Located on the distal end of the needle guard is a needle guard tip 60, through which the needle 24 extends. After the needle guard 30 has been extended to cover the needle 24, the needle guard is locked in its extended position inside the needle housing, and the point of the needle is located inside of the needle guard nose or tip 60.

FIG. 2 is a cross-sectional view of the catheter assembly of FIG. 1. The catheter 50 is seen to extend from the distal end of the catheter hub 52 and is concentric therewith. The catheter may be attached to its hub by any means known in the art, including adhesively or mechanically by means of a metal eyelet. The larger diameter proximal portion 56 of the catheter hub 52 is flanged at its proximal end for connection to an infusion set, and the inner diameter of the proximal portion of the hub is sized to fit over the distal portion of the needle guard tip 60.

The needle 24 is attached to the distal end of the flash chamber 26 of the needle housing with the proximal end of the needle terminating within the chamber. The needle 24 is affixed in place by adhesive or gasketing mechanisms. The needle extends through the needle guard nose 60, the needle hub 52, and the catheter 50, with the point of the needle extending from the distal end of the catheter. The rear of the flash chamber 26 is plugged by a microporous plug 70. The needle guard is seen to extend proximal the rear of the needle housing with the needle guard nose 60 affixed to the distal end of the needle guard at the location of the push-off tab 34. The tubular needle guard surrounds the flash chamber 26, with the base 27 of the flash chamber being located in a longitudinal slot 36 at the bottom of the needle guard. As the needle guard slides in the distal direction to cover the needle it is maintained concentric with the needle housing by the concentric tubular construction of the needle housing and reedle guard and by the tracking of the base 27 of the flash chamber in the needle guard slot 36.

A needle guard nose 60 suitable for use with the needle guard 30 is configured with a proximal end 62 sized to fit in the distal opening 90 of the needle guard 30. The proximal end of the tip is inserted into the needle guard until the shoulder 63 of the tip contacts the side walls of the guard. The central section 64 of the nose 60 has walls on both its internal and external surfaces which maintain their proper sizing to be emplaced within the catheter hub. The distal end 66 of the tip 60 is rounded and open for passage of the needle through the tip. There is a luer fitting 68 on catheter hub 52 for attachment of an infusion set.

As seen in FIGS. 1 and 2, and more especially in FIGS. 3, 3a and 3b, there is disclosed the manual shutoff valve 80 of the present invention. Manual shutoff valve 80 contains three basic components. First, there is pivoting post 82 which is formed on the catheter hub 52. Usually, pivoting post 82 will be an integral part of catheter hub 52. Attached to pivoting post 82 is lever 84. Lever 84 is formed so that it is easy for a finger to be inserted atop lever 84 when in contact with finger grips 22 during operation of the catheter assembly 10. Lever 84 is able to come into contact with catheter 50 through insert hole 86 formed in catheter hub 52.

Operation of the manual shutoff valve 80 is as follows. The user is able to place a finger on lever 84. If the user desires to close the catheter 50, pressure on lever pivoting post 82. The tab 85 formed at right angles to lever 84 moves into insert hole 86 so that catheter 50 is occluded, as best seen in FIG. 3b. If the user then desires to continue with infusion, or to allow blood to flow into flash chamber 26, the user merely removes the pressure on lever 84 so that lever 84 no longer occludes catheter 50. Catheter 50 is formed from a kink-resistant material, such as a polyurethane having a memory so that catheter 50 returns to its normal non-occluded position, and flow is again possible through catheter 50.

The catheter assembly of FIGS. 1, 2 and 3 may be used in the conventional manner by inserting the concentric catheter and needle through the skin of a patient and into a blood vessel. When the point of the needle 24 is properly located in the vessel, a small amount of blood will flow through the needle and into the flash chamber 26. Since the needle housing and guard are made of transparent or translucent polymeric materials, the flow of blood will be readily apparent in the flash chamber.

The needle is then retracted from the vessel and the catheter 50 threaded into the vessel by grasping the finger grips 22 of the housing with the thumb and fingers and pushing the push-off tab 34 in the distal direction with one finger. This motion will push the catheter hub 52 off of the needle guard tip 60 to advance the catheter. As the needle guard begins to extend out from the distal end of the needle housing such that the push-off tab 34 is beyond the reach of the finger of the user, the user may engage the projections 32 with the finger to continue the distal motion of the needle guard. Finally this motion will result in proper threading of the catheter into the vessel and the complete withdrawal of the needle from the patient's body. The needle guard 30 is then advanced to its fullest extension and lock in its protective position. The needle, housing and guard may then be set aside without concern for inadvertent injury to the user or others, and an infusion set is attached to luer fitting 68 in order to begin infusion to the patient.

Of course, at all stages of insertion and removable of the needle, the user may manually override the mechanism by exerting pressure on lever 84, as previously disclosed. After removal of the needle, and during infusion, the user is still able to exert pressure on lever 84 in order to halt infusion into the patient. This newly created device makes the catheter assembly 10 much more user friendly and versatile in its capabilities, both before, during and after insertion and infusion.

The invention may be better understood from the attached claims and their equivalents.

What is claimed is:

1. A catheter assembly comprising:
   a catheter attached to a catheter hub;
   a hollow needle extending into said catheter and catheter hub and removable from said catheter; and
   occludable means on said catheter hub for preventing fluid flow through said catheter, wherein said occludable means includes a lever pivotable about said catheter hub and capable of occluding said catheter;
   and further including means for inserting said lever through said catheter hub and into said catheter.

2. The catheter assembly of claim 1, wherein said catheter and catheter hub are tubular and concentric.

3. The catheter assembly of claim 2, wherein said lever is spring-loaded so that in its normal position said lever does not occlude said catheter.

4. The catheter assembly of claim 3, wherein said lever further includes a tab insertable through said means in said catheter assembly such that such tab occludes said catheter.

5. The catheter assembly of claim 1, wherein said catheter is formed from a material having a memory so that when said occludable means does not occlude said catheter, said catheter returns to a position permitting fluid flow.

6. The catheter assembly of claim 5, where said material is polyurethane.

7. A catheter assembly comprising:
   a needle housing having a hollow needle extending from the distal end thereof;
   a needle guard slideably located within said needle housing and including an aperture at its distal end for passage of said hollow needle therethrough;
   a catheter and catheter hub assembly suitable for mounting on the distal end of said needle guard; and
   means for occluding said catheter through said catheter hub in order to prevent fluid flow through said catheter wherein said occluding means includes a lever mounted on said catheter hub, and capable of occluding said catheter.

8. The assembly of claim 7, wherein said lever is capable of occluding said catheter through a hole in said catheter hub.

9. The assembly of claim 8, wherein said lever is spring-loaded on said catheter hub.

10. The assembly of claim 9, wherein said lever contains a tab located proximal said catheter and capable of occluding said catheter.

11. The assembly of claim 7, wherein said catheter is formed from a material having a memory, such that when not occluded said material remains in a position permitting fluid flow.

12. The assembly of claim 11, wherein said material is polyurethane.

13. The assembly of claim 10, wherein said catheter hub contains a post around which said lever rotates.

* * * * *